United States Patent [19]

Drake et al.

[11] Patent Number: 5,192,265
[45] Date of Patent: Mar. 9, 1993

[54] ADJUSTABLE-RESISTANCE ANTI-SIPHON DEVICE

[75] Inventors: James M. Drake; Richard Fox, both of Toronto; Andre Bahoric, Don Mills, all of Canada

[73] Assignees: HSC Research & Development Limited Partnership, Toronto, Canada; James M. Drake

[21] Appl. No.: 625,268

[22] Filed: Dec. 10, 1990

[51] Int. Cl.⁵ .......................................... A61M 27/00
[52] U.S. Cl. .................................... 604/10; 604/9; 623/66
[58] Field of Search ........................ 604/8-10, 604/247, 153; 623/66; 132/510

[56] References Cited

U.S. PATENT DOCUMENTS

| | | |
|---|---|---|
| 3,889,687 | 6/1975 | Harris et al. ........................... 604/10 |
| 3,901,245 | 8/1975 | Spitz et al. ............................ 604/10 |
| 4,056,095 | 11/1977 | Rey et al. ............................... 623/66 |
| 4,364,395 | 12/1982 | Redmond et al. .................... 604/10 |
| 4,457,752 | 7/1984 | Vadasz ................................. 604/135 |
| 4,867,741 | 9/1989 | Portnoy ................................. 604/10 |
| 5,069,663 | 12/1991 | Sussman ................................. 604/9 |

FOREIGN PATENT DOCUMENTS 2042685 9/1980 United Kingdom ..................... 604/9

*Primary Examiner*—Robert A. Hafer
*Assistant Examiner*—Kerry Owens
*Attorney, Agent, or Firm*—Bell, Seltzer, Park & Gibson

[57] ABSTRACT

An adjustable-resistance anti-siphon device for a cerebrospinal fluid shunt is provided. The device has a substantially rigid housing having an internal cavity which contains a first chamber and a second chamber, the first chamber having at least one flexible wall, an inlet port and an outlet port, the ports passing through apertures in the housing; the second chamber being gas-filled and being in pressure communication with at least a portion of the at least one flexible wall of the first chamber; and gas pressure control means connected to said gas-filled chamber whereby the pressure in said gas-filled chamber may be adjusted.

11 Claims, 2 Drawing Sheets

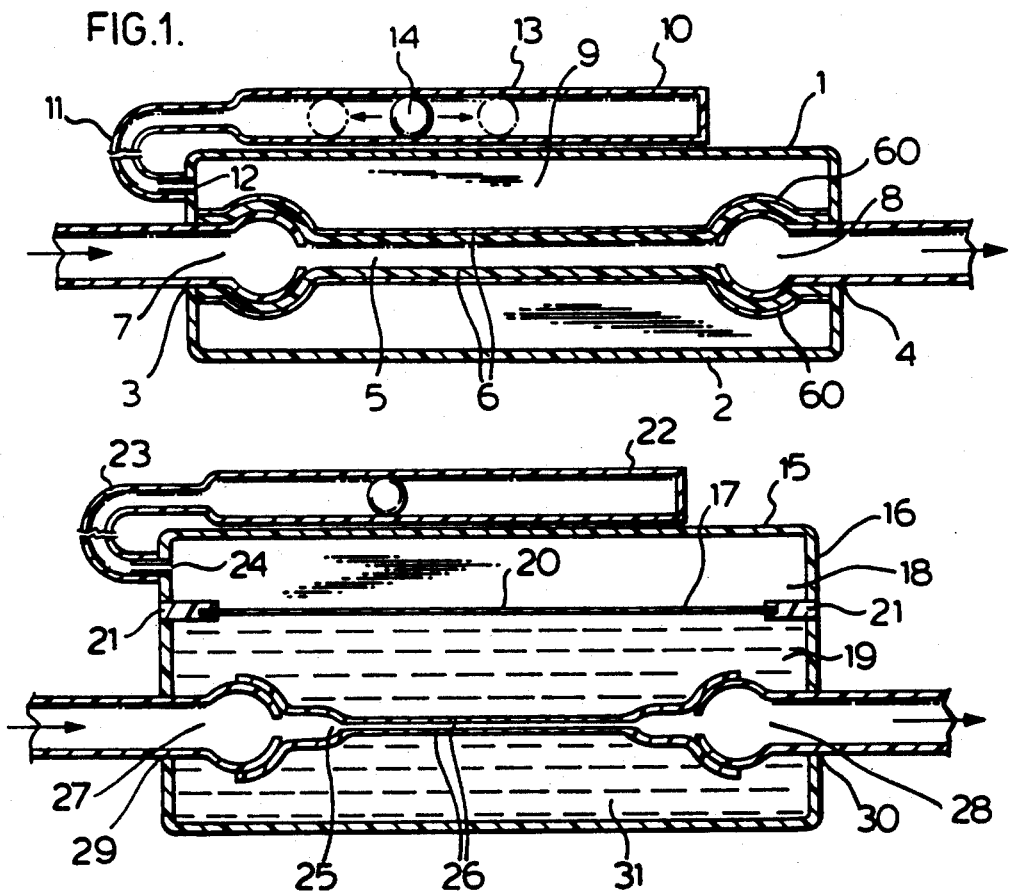
FIG.1.
FIG.2.
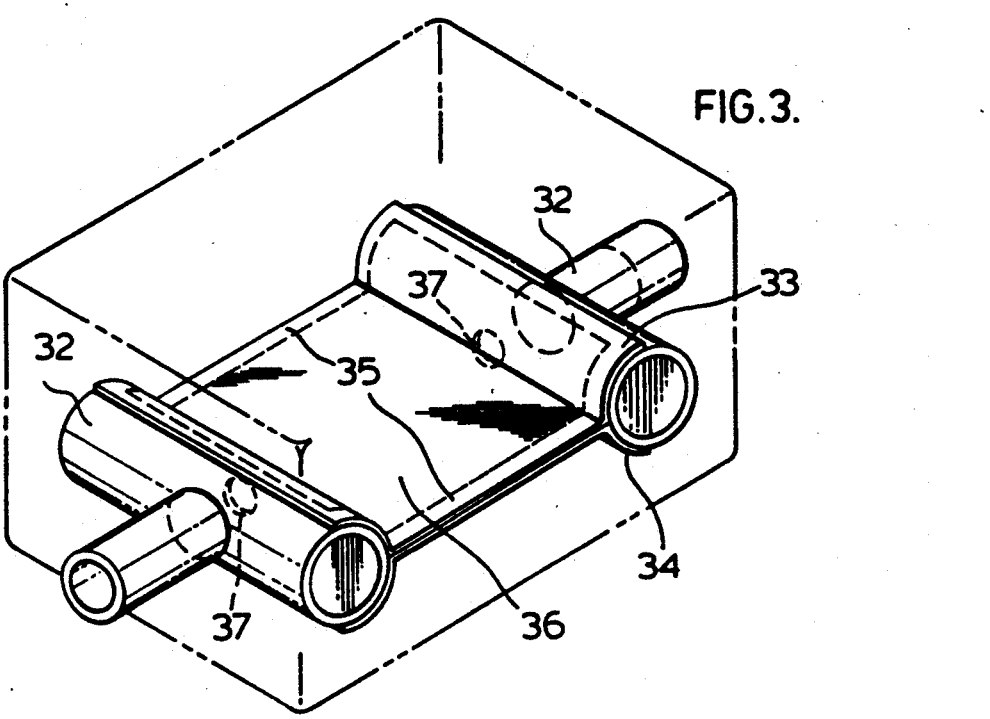
FIG.3.

ADJUSTABLE-RESISTANCE ANTI-SIPHON DEVICE

This invention relates to an adjustable resistance anti-siphon device for use in association with a cerebrospinal fluid shunt system.

In the condition known as hydrocephalus, excess cerebrospinal fluid builds up in the brain and requires the insertion of a drainage system or cerebrospinal fluid (CSF) shunt to divert the excess fluid into another body cavity, for example either the peritoneal cavity or the atrium of the heart, thus relieving pressure on the brain.

When a subject having an implanted CSF shunt assumes an upright position, there is a tendency to siphoning of CSF through the shunt system, with excessive draining of CSF from the brain, which is also undesirable.

There are two anti-siphon devices commercially available at present, the Heyer-Schulte device and the P-S Medical CSF siphon control device. Both of these devices rely on a flexible membrane which closes to shut off CSF flow in response to downstream suction. The flexible membrane forms part of the outer wall of these devices, and since these devices are implanted underneath the skin of the scalp, the devices are subject to pressure from tissue and body fluids and from atmospheric pressure transmitted through the skin.

These devices may be subject to problems arising from interference with their function by scarring or other conditions of the tissue overlying the flexible membrane.

U.S. Pat. No. 3,769,982 discloses, in one embodiment, the Schulte device which has a resilient flexible membrane forming part of the outer wall of the device.

A further embodiment has a flow chamber of resilient material within a body which may have ports allowing communication with body fluids or ma be closed so that a fixed pressure is exerted on the outside of the flow chamber.

None of the prior anti-siphon devices allow control of the resistance to CSF flow through the device independent of ambient pressure in the tissue surrounding the device or adjustment of the resistance to CSF flow to a desired level once the device is implanted.

U.S. Pat. No. 4,781,673 discloses a switching device which may be installed in a CSF shunt, allowing diversion of CSF flow through flow passages of different dimensions, thus providing some degree of regulation of CSF flow rate. The passages are controlled by on/off ball valves which may be opened or closed by external manual manipulation when the device is implanted under the scalp. The presence of mechanical moving parts in contact with the CSF stream gives potential for clogging and mechanical failure. The switching device gives no protection against siphoning.

U.S. Pat. Nos. 4,787,886; 4,766,838; 4,729,762 and 4,557,721 all disclose valve systems for use in CSF shunts which are responsive to pressure differentials between the ventricular space and the remote drainage location or between the epidural space and the remote drainage location, and do not prevent siphoning.

U.S. Pat. No. 4,443,214 discloses a valve device for a CSF shunt in which ventricular fluid pressure must overcome the force exerted by a spring biased valve in order to permit CSF flow through the valve. The force exerted by the metal spring biased valve may be adjusted to one or two different levels by external manipulation of the spring by means of a magnet. This device offers no protection against siphoning. In addition, the presence of magnetic components can interfere with Magnetic Resonance Image scans.

The present invention relates to an adjustable resistance anti-siphon device. According to one aspect of the invention, an adjustable-resistance anti-siphon device for a cerebrospinal fluid shunt comprises a substantially rigid housing having an internal cavity which contains a first chamber and a second chamber, the first chamber having at least one flexible wall, an inlet port and an outlet port, and these ports passing through apertures in the housing. The second chamber is gas-filled and is in pressure communication with at least a portion of the at least one flexible wall of the first chamber and gas pressure control means is connected to the gas-filled chamber whereby the pressure in the gas-filled chamber may be adjusted.

When the gas-filled second chamber of the device of the invention is described as being "in pressure communication" with at least a portion of the at least one flexible wall of the first chamber, what is meant is that the gas-filled chamber is in direct or indirect contact with the at least one flexible wall in such a way that an increase in gas pressure in the gas-filled second chamber causes expansion of the second chamber thereby applying pressure directly or indirectly to the at least one flexible wall of the first chamber; conversely, reduction of pressure in the gas-filled second chamber results in a reduction of the pressure applied to the at least one flexible wall of the first chamber.

The invention, as exemplified by preferred embodiments, is described with reference to the drawings in which:

FIG. 1 is a sectional view of one embodiment according to the invention;

FIG. 2 is a sectional view of a further embodiment of the invention;

FIG. 3 is a partial perspective view of the embodiment of FIG. 2;

Figure 4:
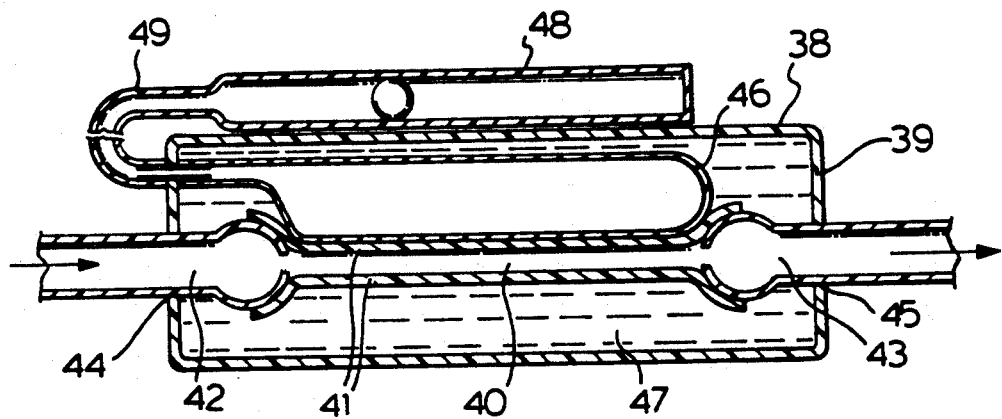
FIG. 4 is a sectional view of a further embodiment of the invention.

FIG. 1 shows one embodiment of an adjustable-resistance anti-siphon device 1 according to the invention. Anti-siphon device 1 has a substantially rigid housing 2 penetrated by apertures 3 and 4. Within the housing 2 is located a chamber 5 having walls 6, an inlet port 7 and an outlet port 8, these ports passing through apertures 3 and 4 respectively in the housing 2.

In the embodiment of the invention seen in FIG. 1, the space within the housing 2 surrounding chamber 5 is filled with gas, forming gas-filled chamber 9, which is connected to gas pressure control means 10 by flexible tubing 11 which passes through a further aperture 12 in housing 2.

At least one of the walls 6 of chamber 5 is flexible and gas impermeable and is in pressure communication with gas-filled chamber 9.

In a preferred embodiment of the invention, both walls 6 are flexible, gas-impermeable and in pressure communication with gas-filled chamber 9.

Gas pressure control means 10 has a flexible, gas-filled pressure control tube 13 containing a ball 14 which fills the lumen of tube 13 to form a gas-tight plug. The ball 14 can be moved within pressure tube 13 by external manipulation or pinching of the tube.

Inlet port 7 is connected to the ventricle-draining catheter of a CSF shunt system by conventional connectors and outlet port 8 is similarly connected to the shunt catheter which delivers drained cerebrospinal fluid to a desired remote body cavity such as the peritoneal cavity or the atrium of the heart, so that CSF enters chamber 5 of the device 1 by inlet port 7 and exits by outlet port 8.

Other embodiments of the invention hereafter disclosed may be similarly connected into a CSF shunt system. The CSF shunt system should also include a one-way or check valve to prevent reverse flow of CSF along the shunt.

The housing 2 may be positioned against the skull and beneath the scalp or in any subcutaneous location along the path of the shunt tubing. Pressure control tube 13 may also be positioned against the skull and beneath the scalp, secured to the tissue of the scalp and connected to housing 2 by flexible tubing 11; it may be placed on top of the housing as seen in the Figures.

The chamber 2 is designed to have minimal resistance to flow at atmospheric pressure at CSF flow rates less than 60 ml. per hour. When fluid pressure in chamber 5 becomes negative with respect to gas pressure in chamber 9, for example due to change of position of the subject having the shunt system implanted, the flexible walls 6 of chamber 5 are drawn together as depicted in FIG. 2 and resistance to CSF flow rises, thus maintaining a constant proximal shunt pressure and preventing overdraining of CSF.

The proximal shunt pressure may be controlled at any desired value by adjustment of the pressure in the gas-filled chamber 9 by pressure control means 10. By sliding ball 14 towards connection tubing 11 by external manipulation of pressure tube 13, pressure is increased in gas-filled chamber 9, causing collapse of the walls 6 of chamber 5 and reduction in CSF flow. If the pressure in gas-filled chamber 9 is decreased by sliding ball 14 away from connection tubing 11, there is less tendency for the walls 6 of chamber 2 to collapse and resistance to CSF flow drops.

FIGS. 2 and 3 show another embodiment of the invention. Anti-siphon device 15 has an essentially rigid housing 16 divided by a wall 17 into a first compartment 18 and a second compartment 19. The wall 17 comprises a gas-impermeable flexible membrane 20 which is attached by supports 21 to housing 16. Compartment 18 is gas-filled and is connected to gas pressure control means 22 by flexible tubing 23 which passes through aperture 24 in housing 16. Gas pressure control means 22 is as described for gas pressure control means 10 of the first embodiment.

Within compartment 19 is located a chamber 25 having flexible walls 26, an inlet port 27 and an outlet port 28, these ports passing through apertures 29 and 30 which penetrate housing 16. Compartment 19 contains an inert fluid 31 surrounding chamber 25.

When fluid pressure in chamber 25 becomes negative with respect to the gas pressure in compartment 18, membrane 20 moves downwards and flexible walls 26 of chamber 25 are drawn together, maintaining proximal shunt pressure as described before.

Proximal shunt pressure may be adjusted as desired by adjustment of the pressure in gas-filled compartment 18 by pressure control means 22 as described before.

Increased pressure in compartment 18 causes flexible membrane 20 to be deflected towards chamber 25 increasing the pressure in compartment 19 and thereby the resistance to CSF flow through chamber 25.

Figure 6A:
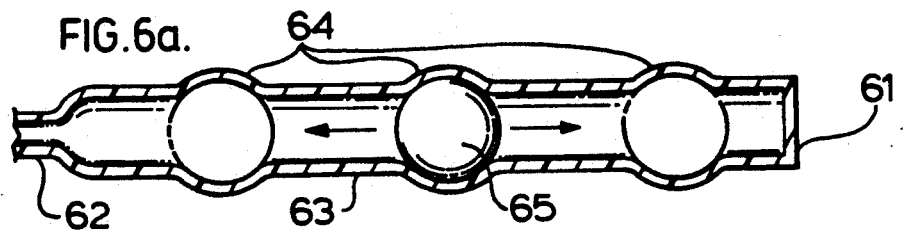
FIGS. 6a and 6b are sectional views of further embodiments of gas pressure control means of the invention.
Figure 6B:
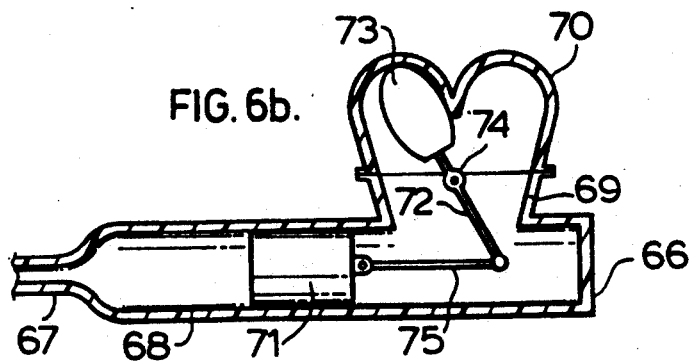

Further embodiments of the invention employ the gas pressure control means of FIGS. 6a and 6b.

In FIG. 6a, gas pressure control means 61 is connected by connection tube 62 to the housing of the device and has a gas-filled flexible pressure control tube 63 having therein a plurality of expanded portions or chambers 64 for accommodation of ball 65. Ball 65 is moved into any one of expanded portions 64 by external manipulation or pinching of tube 63, thereby altering the pressure in the gas-filled chamber connected to tube 63.

In FIG. 6b, gas pressure control means 66, which is connected by tube 67 to the housing of the device, has a gas-filled generally rigid pressure control tube 68 having a side-arm 69 closed by a multi-chambered cap 70 of flexible material. A piston 71 fills the lumen of tube 68 and may be moved within tube 68 by means of lever device 72. When control knob 73 of lever device 72 is moved from one chamber of cap 70 to another by external manipulation of the flexible cap, lever device 72 pivots about pivot point 74 which is attached to side-arm 69 and thereby moves connecting rod 75 and piston 71 backwards or forwards along tube 68 thereby decreasing or increasing the pressure in the gas-filled chamber connected to tube 68.

Other variants of the gas pressure control means will be appreciated by those skilled in the art.

The flexible walls of the chamber through which the CSF flows may be made of any suitable flexible material, a preferred example being silastic sheeting, which for the embodiment of FIG. 1 is coated to render it gas-impermeable, for example by coating it with latex 60.

The flexible walled chamber and its inlet and outlet parts may be of integral construction. Alternatively, individual components may be cemented together as necessary. In the embodiment of FIGS. 2 and 3, as seen best in FIG. 3, T-pieces 32 are formed from silastic tubing, a rectangular sheet of silastic material 33 is cemented along two opposite edges to the upper surfaces of the T-pieces, a second rectangular sheet of silastic material 34 is similarly cemented to the underneath surfaces of the T-pieces, and the two sheets are cemented to each other along their edges 35 to form an internal chamber 36, an inlet to and an outlet from the chamber being provided by appropriate apertures 37 cut in the wall of the silastic tubing opposite the leg of the T-piece.

The housing of the device of the invention may be of any material of suitable rigidity which can be implanted within a human. Suitable examples are acrylate, methyl methacrylate, nylon, teflon or metal such as stainless steel. The gas-filled chamber or compartment of the device is preferably filled with air.

It is to be understood that all tubing or connections passing through apertures in the housing of the device form a fluid-tight seal with the housing, for example being sealed with silicone sealant.

The flexible gas-impermeable membrane of the second embodiment is conveniently a latex membrane and the inert fluid surrounding the flexible-walled chamber is preferably sterile water, sterile physiological saline or glycerine.

The flexible pressure tube of the pressure control means may be made of silastic material coated with latex to render it gas impermeable.

The connection between the gas pressure control means and the gas-filled chamber of the device may be of any suitably flexible and gas-impermeable material.

The ball or piston of the pressure control means may be of a radio-opaque material eg. barium-impregnated plastic or nylon for detection by radiography. A radio-opaque scale may also be applied to the pressure control tube.

Other suitable material for components of the device will be known to those skilled in the art.

FIG. 4 shows a further embodiment of the invention. Anti-siphon device 38 has a substantially rigid housing 39 within which is located a chamber 40 having flexible walls 41, an inlet port 42 and an outlet port 43, these ports passing through apertures 44 and 45 which penetrate the housing 39.

Also within housing 39 is a gas-filled balloon 46 which is in contact with a portion of the flexible walls 41 of chamber 40. The housing 39 is filled with an inert fluid 47 which surrounds the exterior of the balloon 46 and the flexible-walled chamber 40. The gas-filled balloon is connected to a gas pressure control means 48 by flexible connection 49. Pressure in gas-filled balloon 46 may be adjusted by gas pressure control means 48 as described before. Increased pressure within gas-filled balloon 46 or reduced pressure in chamber 40 causes the balloon to expand and press against flexible-walled chamber 40 thereby increasing resistance to CSF flow through the chamber.

The inert fluid 47 may preferably be water, saline or glycerine, as described before, and the balloon is preferably a latex balloon filled with air.

Figure 5:
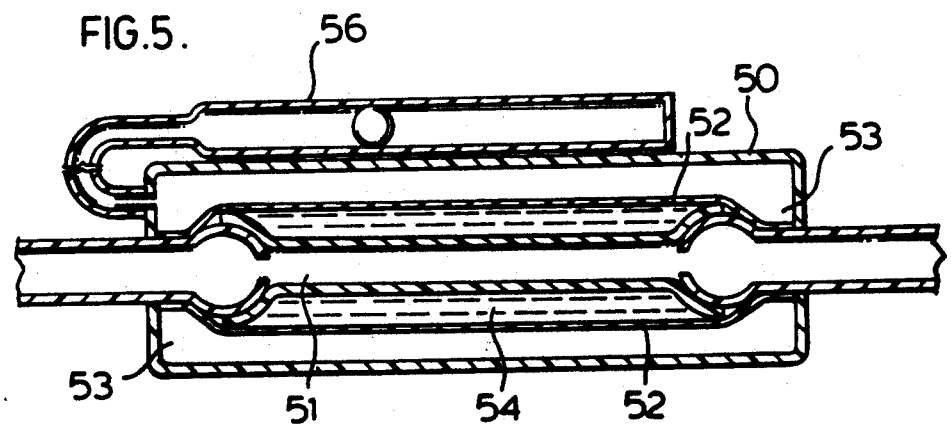
FIG. 5 is a sectional view of still another embodiment of the invention.

The embodiment of FIG. 5 has a housing 50 containing a flexible-walled chamber 51 as described for the embodiment of FIG. 4. The chamber is surrounded by a latex bladder 52 which isolates the chamber 51 from gas-filled compartment 53. The space between the latex bladder 52 and the walls of chamber 51 is filled with an inert fluid 54 as described before. Gas-filled compartment 53 is connected by flexible connection 55 to suitable gas pressure control means 56. Increased pressure in gas-filled compartment 53 squeezes latex bladder 52 and thereby increases pressure on the walls of chamber 51 giving increased resistance to CSF through the chamber.

In the embodiments of FIGS. 2,4 and 5, as previously described for the embodiment of FIG. 1, the chamber of the device through which CSF flows has at least one flexible wall in pressure communication with the gas-filled chamber; in preferred embodiments, both walls of the chamber are flexible and in pressure communication with the gas-filled chamber.

The device of the invention has relatively few components and is of simple construction, making for greater reliability in use.

Since the CSF flow chamber of the device of the invention is enclosed within a rigid housing, the functioning of the device is unaffected by external pressure in the surrounding tissue and is independent of scarring or other tissue conditions under the scalp which have tended to render existing anti-siphon devices unsatisfactory.

Furthermore, the device of the invention allows for adjustment of the resistance to CSF flow to a desired value by external manual adjustment, which is not possible with any previously known anti-siphon device. In a preferred embodiment of the device, as seen in FIG. 1, the resistance to CSF flow may be adjusted continuously to any value within a desired range.

The flexible-walled chamber of the device gives excellent compliance between the pressure set in the gas-filled chamber or compartment and the resulting pressure within the shunt system.

Previously available anti-siphon devices require an increase in the proximal pressure to maintain the same CSF flow rate in the face of negative distal pressures. With the device of the present invention, proximal shunt pressure remains constant for a constant CSF flow rate regardless of the distal catheter height.

Although only certain embodiments of the present invention have been described and illustrated, the present invention is not limited to the features of these embodiments, but includes all variations and modifications within the scope of the claims.

We claim:

1. An adjustable-resistance anti-siphon device for a cerebrospinal fluid shunt comprising a substantially rigid housing having an internal cavity which contains a first chamber and a second chamber, said first chamber having at least one flexible wall, an inlet port and an outlet port for inflow and outflow respectively of cerebrospinal fluid, said ports passing through apertures in said housing;

said second chamber being gas-filled and being in pressure communication with at least a portion of said at least one flexible wall of said first chamber; and gas pressure control means connected to said gas-filled chamber whereby the pressure in said gas-filled chamber may be adjusted.

2. An adjustable-resistance anti-siphon device in accordance with claim 1 wherein said at least one flexible wall of said first chamber is gas-impermeable and the portion of said internal cavity which surrounds said first chamber is gas-filled and forms said second chamber.

3. An adjustable-resistance anti-siphon device in accordance with claim 1 wherein said second chamber comprises a gas-filled balloon in contact with said at least one flexible wall of said first chamber, and said internal cavity further contains an inert fluid surrounding said first and second chambers.

4. An adjustable-resistance anti-siphon device in accordance with claim 1 wherein said internal cavity is divided into first and second compartments by a wall at least a portion of which comprises a flexible gas-impermeable membrane; said first chamber is located within said first compartment, said first compartment further containing an inert fluid surrounding said first chamber; and said second compartment is gas-filled and forms said second chamber.

5. An adjustable-resistance anti-siphon device in accordance with claim 1 wherein said first chamber is surrounded by a flexible gas-impermeable membrane, the space between said first chamber and said surrounding membrane contains an inert fluid and the portion of said internal cavity exterior to said surrounding membrane is gas-filled and forms said second chamber.

6. An adjustable-resistance anti-siphon device in accordance with any of claims 1 to 5 wherein said first chamber has two opposed flexible walls.

7. An adjustable-resistance anti-siphon device in accordance with any of claims 1 to 5 wherein said gas pressure control means comprises a gas-filled compartment wherein the pressure is altered by altering the volume of said compartment.

8. An adjustable-resistance anti-siphon device in accordance with any of claims 1 to 5 wherein said gas pressure control means comprises a gas-filled pressure tube of flexible material connected to said gas-filled second chamber, said pressure tube containing a ball which fills the lumen of said pressure tube to form a gas-tight plug and said ball being movable within said pressure tube by external manipulation thereby altering the pressure in said gas-filled chamber.

9. An adjustable-resistance anti-siphon device in accordance with any of claims 1 to 5 wherein said gas pressure control means comprises a gas-filled pressure tube of flexible material connected to said gas-filled second chamber, said tube having a plurality of expanded portions therein, said tube containing a ball which is movable within said tube by external manipulation to as to lodge said ball in any of said expanded portions of said tube thereby altering the pressure in said gas-filled chamber.

10. An adjustable-resistance anti-siphon device in accordance with any of claims 1 to 5 wherein said gas pressure control means comprises a gas-filled pressure tube connected to said gas-filled second chamber, said tube having a side-arm closed by a multi-chambered cap of flexible material, said pressure tube containing a piston which fills the lumen of said tube, said piston being movable within said tube by means of a lever device attached to the connecting rod of said piston, said lever device being pivotable about a pivot point attached to said side-arm and having a control knob which occupies a chamber of said multi-chambered cap and is movable from one said chamber to another by external manipulation of said flexible cap thereby pivoting said lever device about said pivot point and moving said piston along said pressure tube thereby altering the pressure in said gas-filled chamber.

11. An adjustable-resistance anti-siphon device in accordance with any of claims 1 to 5 wherein said anti-siphon device is connected at said inlet port to a ventricle-draining catheter for draining cerebrospinal fluid from a brain ventricle and at said outlet port to a shunt catheter positioned so as to deliver cerebrospinal fluid to a remote body cavity.

* * * * *

UNITED STATES PATENT AND TRADEMARK OFFICE
CERTIFICATE OF CORRECTION

PATENT NO. : 5,192,265
DATED : March 9, 1993
INVENTOR(S) : James M. Drake, Richard Fox, Andre Bahoric It is certified that error appears in the above-identified patent and that said Letters Patent is hereby corrected as shown below:

On The Cover Page - Item [73]

Assignees: Delete "James M. Drake"

Signed and Sealed this

Twenty-eighth Day of December, 1993

Attest:

BRUCE LEHMAN

Attesting Officer     Commissioner of Patents and Trademarks